United States Patent [19]

Quate

[11] 4,430,897

[45] * Feb. 14, 1984

[54] ACOUSTIC MICROSCOPE AND METHOD

[75] Inventor: Calvin F. Quate, Stanford, Calif.

[73] Assignee: The Board of Trustees of the Leland Stanford University, Stanford, Calif.

[*] Notice: The portion of the term of this patent subsequent to May 19, 1998 has been disclaimed.

[21] Appl. No.: 263,551

[22] Filed: May 14, 1981

[51] Int. Cl.³ .................... G01N 25/72; G01N 29/00
[52] U.S. Cl. ........................................ 73/606; 73/643; 374/5
[58] Field of Search ................. 73/606, 607, 643; 374/5, 44, 45, 57

[56] References Cited

U.S. PATENT DOCUMENTS

| 3,008,029 | 11/1961 | Davis et al. | 374/57 |
| 4,011,748 | 3/1977 | Bond et al. | 73/618 |
| 4,012,950 | 3/1977 | Kompfer et al. | 73/618 |
| 4,255,971 | 3/1981 | Rosencwaig | 73/606 |
| 4,267,732 | 5/1981 | Quate | 73/606 |

Primary Examiner—Herbert Goldstein
Attorney, Agent, or Firm—Flehr, Hohbach, Test, Albritton & Herbert

[57] ABSTRACT

An acoustic microscope and method are disclosed in which an object under investigation is excited by two energy sources. Acoustic waves are propagated from the heated area of the object and the waves are detected and analyzed.

31 Claims, 7 Drawing Figures

ACOUSTIC MICROSCOPE AND METHOD

The Government has rights in this invention pursuant to Contract F4960-78C-0098 awarded by the Air Force Office of Scientific Research.

This invention relates generally to an acoustic microscope and method and more particularly to an acoustic microscope in which the object under axamination is excited with two energy sources one of which introduces the primary energy.

This application is related to my copending application Ser. No. 964,613, filed Nov. 29, 1978, entitled ACOUSTIC MICROSCOPE AND METHOD, now U.S. Pat. No. 4,267,732.

In said copending application there is described an apparatus and method for microscopic imaging and spectroscopy. There are disclosed a plurality of devices for exciting an object of interest by heating so that acoustic waves are propagated from the heated area of the object. The devices used for exciting or heating include lasers, electron beam, x-ray sources, microwave generators, ultra-violet sources and electric current generators. The acoustic waves generated at a localized heated region propagate from the heated region of the object and are detected by an acoustic lens focused on the object of interest at a localized region to detect only acoustic waves generated from the localized region of the object of interest. The object of interest and acoustic wave detector are moved with respect to each other to scan a raster pattern. The magnitude of the detected acoustic waves and the corresponding raster pattern of the object are recorded and may also be displayed on a cathode ray tube to provide a visual image of the object. In addition, the frequency of the exciting electromagnetic radiation that excites the object can be varied so that both the absorption spectra and the Raman frequency mode of the object can be determined.

In 1975 R. A. Lemons and C. F. Quate invented a scanning acoustic microscope. In this microscope a high frequency plane acoustic wave is focused by an acoustic lens to scan an object located at a focal point in the lens. The incident acoustic waves are either transmitted through or reflected by the object at the selected region. In either case the acoustic waves are thereafter recollimated by a second acoustic lens and detected with a piezoelectric detector. The object is scanned and the detected signals are displayed on a cathode ray tube scanned in synchronism to provide a visual display of the object. This device is further described in the Lemons and Quate U.S. Pat. No. 4,028,933 entitled "Acoustic Microscope", dated June 14, 1977.

There is a great need in the semiconductor industry to detect or observe the resistive heating of thin film conductors used in integrated semiconductor devices. It is also important to be able to determine the adhesion of aluminum or other metal films to the silicon or other substrate. The integrated circuits including the films might be destroyed by localized heating if there is poor adhesion.

There is also a need to be able to trace the current flow in an integrated circuit. For example, it would be advantageous to be able to apply pulses to an integrated circuit and then scan the circuit with an acoustic detector synchronized or strobed with the pulses to detect the pulses by the heat which they generate as they travel through different portions of the circuit. However, in general, the pulses are not of sufficient magnitude to generate thermal and acoustic waves as they travel along the metal film. Pulses of sufficient amplitude to generate thermal or acoustic waves would destroy the associated circuits.

In other applications it is desirable to be able to sense localized heating which generates acoustic waves below detection threshold. To be able to detect such localized heating would permit use of a well defined low intensity beam which would provide improved resolution.

It is an object of the present invention to provide an acoustic microscope and method which permits the detection of heat generated acoustic signals which are below threshold.

It is another object of the present invention to provide an acoustic microscope and method in which the object of interest is simultaneously heated with energy from two sources with the combined energy being of sufficient magnitude to generate detectable acoustic waves or to modify acoustic waves reflected from the object at the heated region.

It is annother object of the present invention to mix an intense beam of energy with a weak source of energy and detect the mixed acoustic output and monitor the energy from the weak source.

These and other objects of the invention are achieved by an acoustic microscope and method in which the object of interest is excited or heated by a first energy source in the region of interest and simultaneously with low energy from a different source and the effects of heating at a localized region from both sources is sensed and processed to provide information indicative of the low energy heating at a localized region.

The foregoing and other objects of the invention will be more clearly understood from the following description taken in connection with the accompanying drawings.

Figure 1:
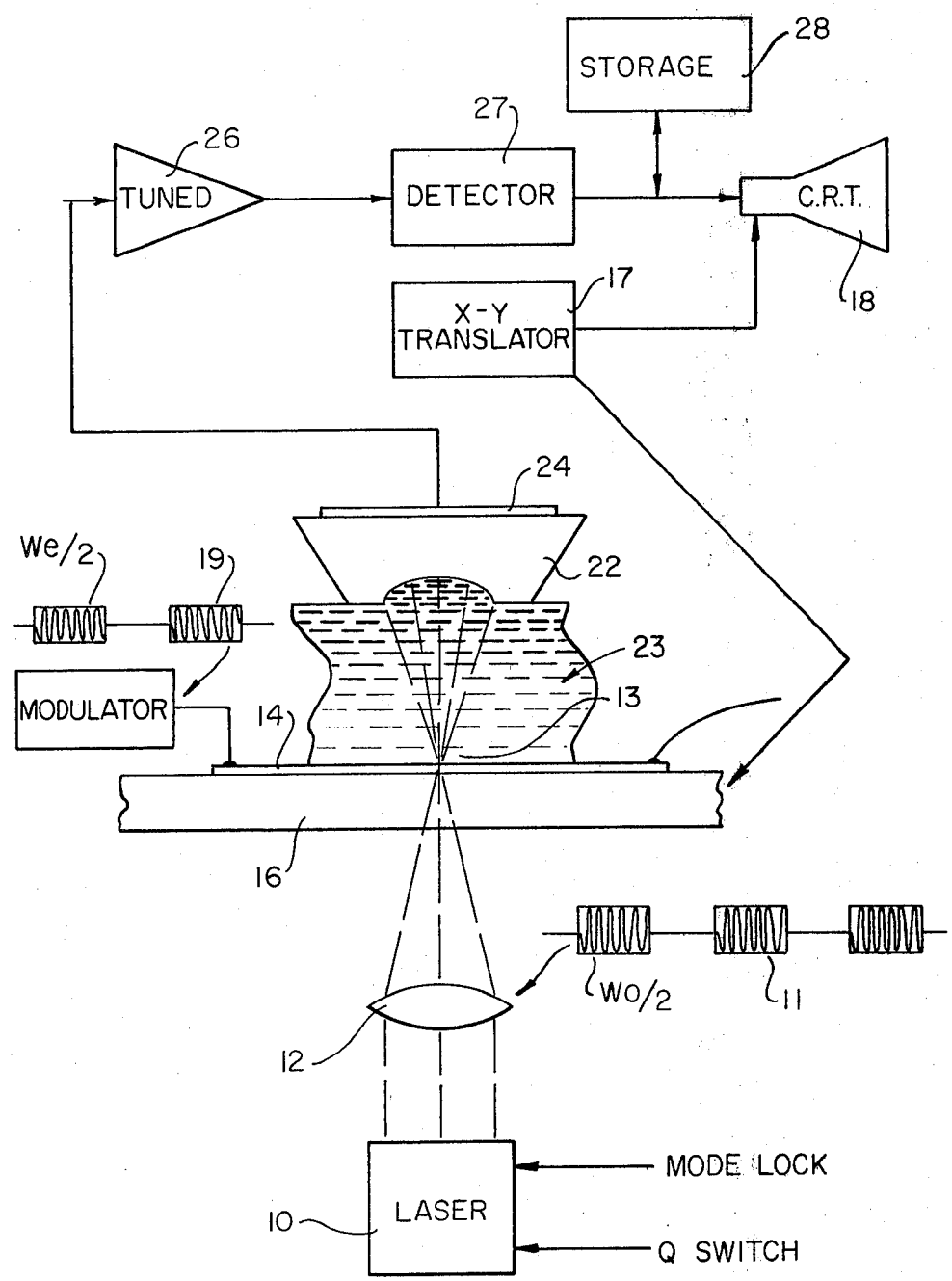
FIG. 1 shows an acoustic microscope system for detecting current pulses traveling in an integrated circuit.
Figure 6:
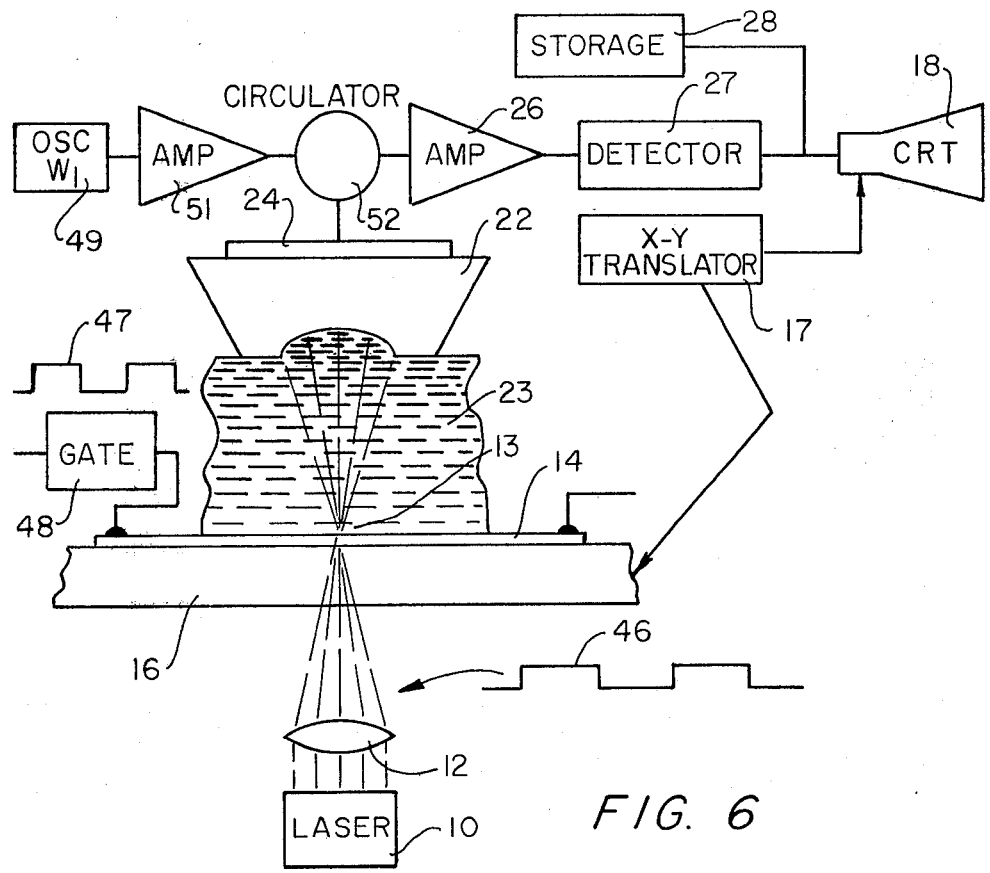
FIG. 6 shows an acoustic microscope system similar to that of FIG. 1 in which modulated reflected acoustic waves are detected.

FIG. 1 illustrates one embodiment of an acoustic microscope in accordance with the present invention. This embodiment includes a laser 10 which excites the film of interest so that a localized area is heated and acoustic waves are propagated therefrom or incident acoustic waves modified, as shown in FIG. 6. The acoustic waves result from the thermoelastic coupling between the light from the laser and the object of interest and have a frequency which is determined by the modulation envelope $\omega_o/2$ of the optical beam. An nd: YAG laser having an output wavelength of 1.06 micrometers can be used. In one embodiment the laser is Mode Locked and Q-switched; the mode locking causes the laser to radiate narrow band pulses, the Q-switching determines the modulation envelope and forms the pulses into bursts 11. The optical output from the laser may, for example, consist of packets of light 200 nsec in duration which a repetition frequency of 1 MHz. Within each packet the pulses in the Mode Locked pulse train are 20 nsec in width with a repeat frequency of 900 MHz.

The modulated input can also be obtained by employing an optical modulator in the beam path or by modulating the laser input, externally or internally, with an r-f carrier. Furthermore the input energy can be from other sources such as an electron gun, x-ray tube or microwave generator.

The output of the laser is directed towards an objective lens 12 which focuses the light to a focal point 13 on the thin film 14. A microscope objective lens (NA=2.25) can focus the optical beam from the laser to a diameter of approximately 2 micrometers. The thin film is mounted on a transparent substrate 16 such as quartz or sapphire. The substrate may be silicon if the laser operates in the infrared where the silicon is transparent. The assembly including the film is moved through the focal point 13 in a raster scanning pattern that is parallel to the X-Y plane by X-Y translator 17. The X-axis translator is a mechanical stage that slowly moves the substrate in one direction. The translator is also connected to a potentiometer (not shown) which converts the X position of the same into an electrical output signal. The sample is also moved in the focal plane along the Y-axis by a Y-axis translator. This translator may comprise an audio speaker (not shown) that moves the sample rapidly back and forth. The audio speaker can be driven in a reciprocal manner by an audio oscillator. The audio oscillator also provides an electrical output signal indicating the position of the sample along the Y-axis. The X and Y position signals were fed to conventional image retention oscilloscope or CRT 18 so that the raster scan of the CRT is synchronized with the raster scan motion of the substrate 16 through the focal point 13. A suitable X-Y translating apparatus is shown and described in U.S. Pat. No. 4,028,933. Thus, the sample focal point is radiated with optical beam at a first frequency $\omega_o/2$ at a pulse rate of approximately 1 MHz.

In accordance with the present invention the film is also subjected to current pulses 19 having a frequency $\omega_e/2$, for example, of 400 MHz at a repetition frequency of approximately 1 MHz. The coincidence of the optical pulses and current pulses of focal point 13 heats the localized region and generates acoustic waves. The acoustic waves are at a frequency corresponding to multiples of the frequences, $\omega_o/2$ and $\omega_e/2$, and to the sum and difference of these frequencies since heating is a non-linear function of the input. The output acoustic pulses from the region 13 are at the mixed frequency of the current and optical energy. These acoustic waves are incident on the concave surface of the acoustic lens 22. The acoustic lens collimate the waves into plane waves which can be detected without substantial distortion. The acoustic lens may be a sapphire crystal with a receiving area having a radius, for example, of 200 micrometers. The lens is selected for the frequency. Larger lens are used at lower frequencies and smaller lens at higher frequencies. A fluid 23 is provided between the lens and film to transmit the acoustic waves. The acoustic lens detects the acoustic waves having frequencies in the range of 50 MHz to 1000 MHz, for example, and has a focal point with a diameter of approximately 1 micrometer at the higher frequencies. The acoustic lens is coated with a quarter wavelength layer of glass (not shown) to minimize reflection at the lens surface. The acoustic lens may be positioned in the apparatus so that its focal point is coincident with the focal point 13 of the optical lens 12. This arrangement ensures that the acoustic pulse train which is generated at the focal point 13 is received by the acoustic lens 22. Since the heating is localized and lens need not be confocal it need only receive the energy from the localized region.

As described above, the mixed acoustic waves are propagated through a liquid 23 such as water. Other fluids such as methanyl, liquid nitrogen and liquid helium can be used. The liquid permits the object of interest to be moved with respect to the acoustic lens while transmitting acoustic waves across the path between the object and the lens. The acoustic plane waves collimated by the acoustic lens 22 are converted into electrical signals by a transducer 24. The transducer includes a thin layer of gold deposited on the rear surface of the acoustic lens followed by sputtered layers of zinc oxide and a second outer layer of gold. A combination of these three layers forms a capacitor with a zinc oxide dielectric. In a preferred embodiment transducer has a response near 1000 MHz.

The output signals from the transducer 24 coupled to lens 22, FIG. 1, are passed to a tuned amplifier 26, tuned to the sum or difference frequency, which increases their signal strength. The output of the amplifier is connected to a detector 27 which may be a tunable radio receiver. The detector converts the amplifier output into a direct current signal level which is used to modulate the intensity of the beam in the CRT 18. The signal level is also recorded in the storage device 28 which may comprise magnetic tape or discs.

A control signal from the X-Y translator 17 controls the position of the CRT beam so that as the object is scanned the CRT is scanned and the beam forms an image displayed on the CRT 18.

In accordance with the present invention, the combination makes possible the detection of the heating caused by the current pulses, which heating would generate acoustic waves below threshold. However, by the mixing of the acoustic waves generated by the optical and electric heating, the electric heating can be detected.

More particularly, the power $I_{ab}$ absorbed in the film consists of two parts $I_o$, the power absorbed from the optical beam modulated at the frequency $\omega_o/2$ and $I_e$ the electric power dissipated in the film through resistive heating by current at the frequency $\omega_e/2$. Thus, $$I_{ab} = Re(I_o e^{j\omega_o t} + I_e e^{j\omega_e t}) \tag{1}$$

Since the acoustic power can be a non-linear function of the absorbed energy both sum and difference frequencies are encountered. Assume also that I is much small than $I_o$ and the non-linearlity can be represented by a square law then the squared term products are of the form $$I_o^2 e^{2j\omega_o t}, \quad I_o I_e e^{j(\omega_o + \omega_e)t}$$

and $$I_o I_e e^{j(\omega_o - \omega_e)t}$$

It is the second and third terms that are of interest. In the above example with the optical beam modulated at 600 MHz and the electric current at 400 MHz, one looks for sound at the sum frequency of 1000 MHz or the difference frequency of 200 MHz. When proper account is taken of the exponentials in the product, the power is given by $$I_{ac} = 5 \times 10^{-17} I_o I_e \qquad (2)$$

for the acoustic intensity at $\omega_o + \omega_e = 1000$ MHz. There will be an equal amount at $\omega_o - \omega_e = 200$ MHz and a large component at $2\omega_o = 1200$ MHz.

It is seen that the power generated by the current pulses can be rather small if $I_o$, the power generated by the optical beam, can be made large enough. Thus, one can trade optical heating for electrical heating and in this way produce a system that will permit detection of electrical heating at very low levels such as would be generated by pulses in an integrated circuit. By synchronizing the pulses from the electric current source and from the laser and the position of the X-Y translator, one can strobe the surface of the substrate and detect the position of current pulses within the integrated circuit at different times.

An example demonstrates that the present invention can detect low level heating. First, how large a value of $I_o$ can be used? This will be limited by the damage sustained by the film. A level of 20 megawatt/sm² is believed to be a safe value that will not produce appreciable damage. Therefore $$I_o = 2 \times 10^7 \text{ watt/cm}^2 = 2 \times 10^{11} \text{ watts/mtr}^2 \qquad (3)$$

What is the maximum value of $I_e$? This will be limited by the resistivity of the metal film ($2.7 \times 10^{-6}$ Ω-cm for Al) and by the maximum current density. The maximum current density for metal film is $J = 5 \times 10^6$ amps/cm² for the short term. For a film of thickness t, width W at length L, the dissipated power is $\frac{1}{2}I^2 R$ or $$P_e = \frac{1}{2}\rho(L/Wt)J^2 W^2 t^2 = \frac{1}{2}\rho J^2 t(WL)$$

and $$I_e = P_e/WL = \frac{1}{2}\rho J^2 t \qquad (4)$$

For an aluminum film 0.5 microns thick $$I_e = 17 \ \mu W/\mu m^2 \sim 2 \times 10^7 \text{ watt/mtr}^2.$$

With these numbers we have from (2)

$$I_{ac} = 5 \times 10^{-17} \times 2 \times 10^{11} \times 2 \times 10^7 \text{ watts/mtr}^2$$

or $$I_{ac} = 200 \text{ watts/mtr}^2 \qquad (5)$$

The total acoustic power for an acoustic beam focused to 10 $\mu m^2$ (3 $\mu m$ dia) is $$P_{ac} = 200 \times 10^{-11} = 2 \times 10^{-9} \text{ watts} = 2 \times 10^{-6} \text{ milliwatts}$$

Thus, the acoustic power at the aluminum-water interface is −57 dBm. This should be detectable with our presently available instrumentation.

Figure 2:
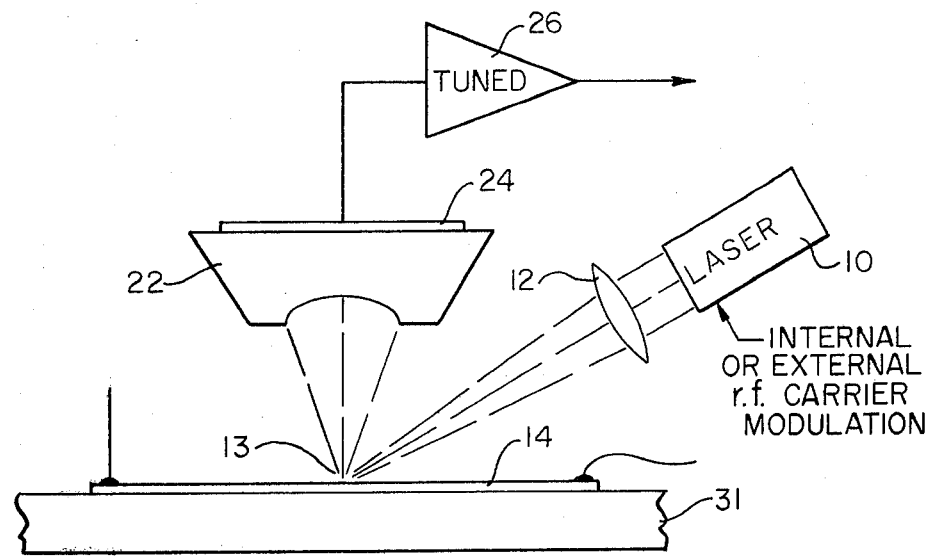
FIG. 2 is a schematic view showing another acoustic microscope for detecting currents in an integrated circuit.

Heating can be detected on a film which is mounted upon an opaque substrate such as substrate 31, FIG. 2. In this instance, the pulsed laser is arranged to focus onto the upper surface of the film to provide the localized heating.

In this embodiment the laser is modulated by an r-f carrier. In other respects the embodiment of FIG. 2 operates like the embodiment of FIG. 1 and like reference numbers have been applied to like parts.

Figure 3:
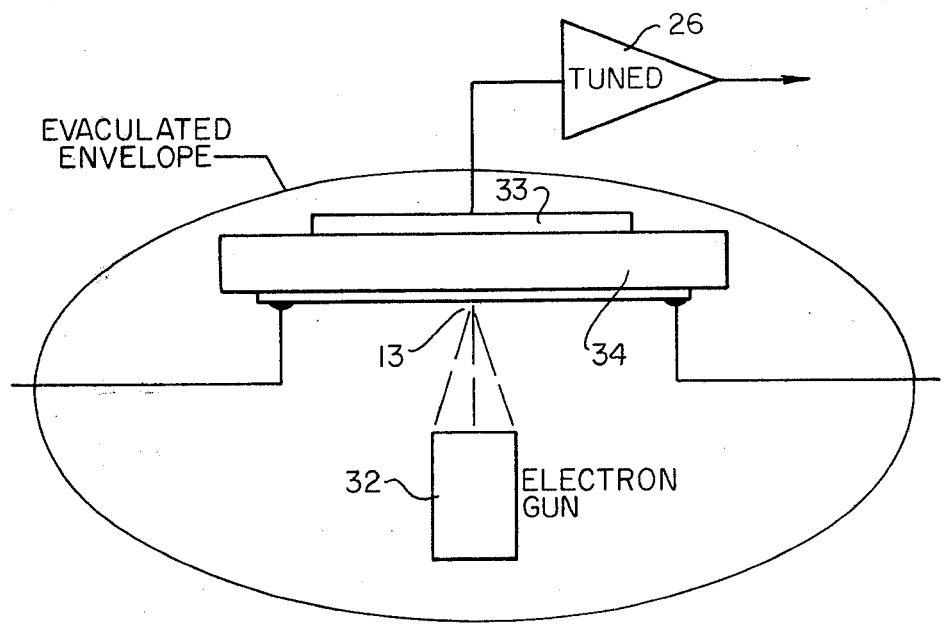
FIG. 3 shows still another acoustic microscope in accordance with the present invention.

The principle of mixed signals of different frequencies and amplitude can be employed in the embodiment in which the acoustic wave transducer is not focused such as shown in FIG. 3. In the embodiment of FIG. 3 the strong heating source is a highly focused r-f modulated electron gun 32. The receiving transducer 33 is mounted to receive the acoustic waves traveling through the substrate 34.

Figure 4:
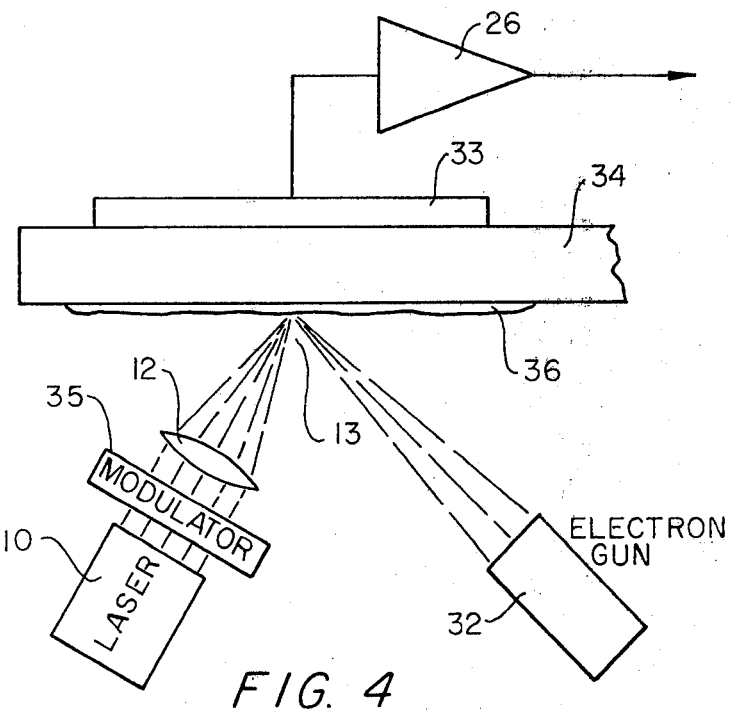
FIG. 4 shows an acoustic microscope for inspecting a specimen.

In the embodiment of FIG. 4 there is shown a combination of optical and electron beams for heating a localized region of a specimen 36. In this example the laser output is modulated by a modulator 35 to form modulated pulses. The advantage of FIG. 4 is that the electron beam can be a low intensity, highly focused electron beam and the heating from the beam can be detected via the mixing of the acoustic waves generated by the laser heating.

Figure 5:
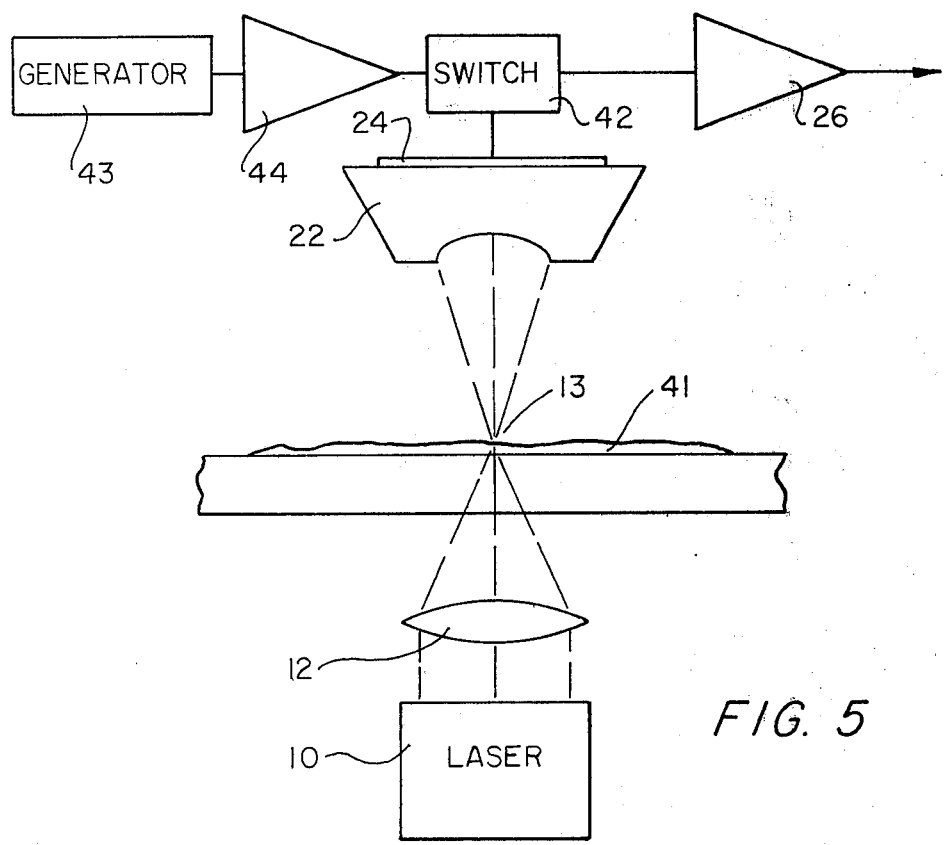
FIG. 5 shows still another acoustic microscope for inspecting a specimen including a combination of optical and acoustic excitation.

In the embodiment of FIG. 5 the specimen 41 is heated with a laser beam and is also energized by a low energy acoustic beam from the transducer 22 via the switch 42 connected to generator 43 by amplifier 44. The switch acts as a circulator to apply energy from the amplifier 44 to the transducer to generate and apply acoustic waves to the specimen which are reflected and collected by the lens converted and passed to amplifier 26. Thus, the low energy heating source may be acoustic.

FIG. 6 shows an acoustic microscope similar to that shown in FIG. 1. However, the laser is pulsed to form pulses 46 which are not modulated. Similarly the electrical pulses 47 are formed by a gate 48. The transducer 22 serves as a transmitter of acoustic waves responsive to energy at frequency $\omega_1$ from oscillator 49 amplified by amplifier 51 and applied from circulator 52. The energy from the laser and the current will alter the temperature of the sample. This, in turn, will alter the elastic parameters of the sample. This acts on the reflected incident acoustic energy which is transduced by transducer 22 and applied to amplifier 26. The output to tuned amplifier 26 is then at frequency $\omega_1$. If the apparatus is operated as with the pulses 46 or 47 modulated at an r-f freuency $\omega_o$ or $\omega_e$ or $\omega_1 \pm \omega_e$.

Figure 7:
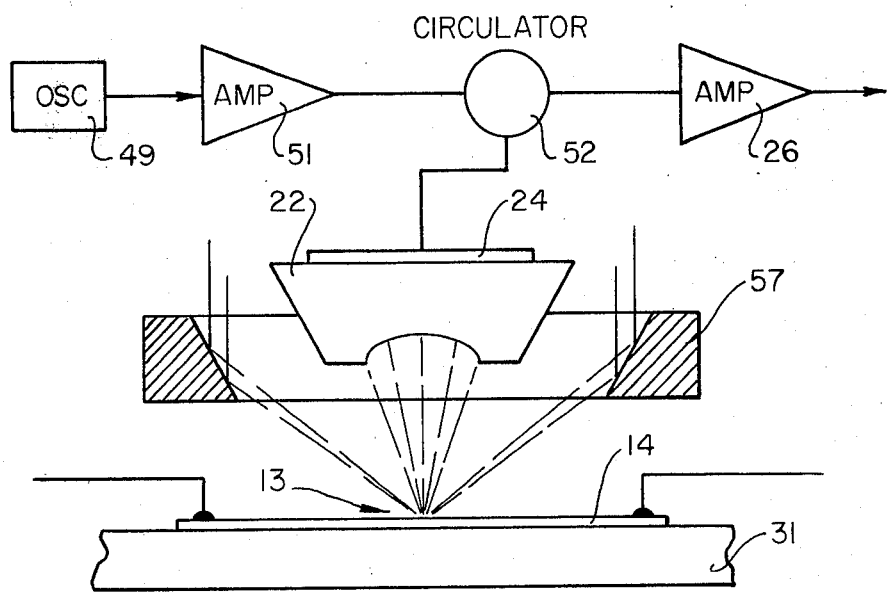
FIG. 7 shows an acoustic microscope similar to that of FIG. 5 in which modulated reflected acoustic waves are detected.

FIG. 7 is similar to the system shown in FIG. 2 and like reference numerals are applied to like parts. The system shown employs the modulation of incident acoustic waves by the heated sample as described in connection with FIG. 6. Thus, like numerals have been applied to like parts. The incident optical energy is applied by a torroidal reflector 57 whereby it is confocal with the acoustic beam.

Thus, there is disclosed an apparatus and method in which there is mixed an intense beam with a weaker beam or source of heating to permit monitoring the heating caused by the weak source. This permits the use of a high intensity source of heating to permit monitoring the heating caused by the weak source. This permits the use of a high intensity source which might damage the object if operated at an intensity to generate detectable acoustic waves or to permit use of a highly focused low intensity beam. It is apparent that the frequencies $\omega_o$ or $\omega_e$ can be zero; that is a d.c. current may be used or an unmodulated energy source (laser, electron gun, etc.) may be used. The heating by the weak and strong energy is alternatively detected by employing a reflected acoustic beam.

What is claimed is:

1. An acoustic microscope comprising
   first means for heating an object of interest so that the object thermally expands responsive thereto,
   second means for heating the object of interest at the region of interest so that the object at the point of interest thermally expands responsive thereto, the thermal expansion by both sources provides output acoustic waves and means for sensing said acoustic waves and providing an output signal representative of the expansion due to the heating by said first and second heating means.

2. An acoustic microscope as in claim 1 in which said means for sensing the acoustic waves generated by the expansion at the region of interest comprises an acoustic transducer which provides an output electrical signal.

3. An acoustic microscope as in claim 2 in which said first means for heating heats the object at a first frequency and said second means heats the object at the region of interest at a second frequency.

4. An acoustic microscope as in claim 3 in which said means for receiving the generated acoustic waves provides an output representative of the sum or difference frequency of said acoustic waves.

5. An acoustic microscope as in claim 3 in which one of said heating frequencies is zero.

6. An acoustic microscope as in claim 3 when at least one of said heating means is focused on the point of interest.

7. An acoustic microscope as in claim 6 in which said means for receiving said generated acoustic waves and providing an output signal is focused at said point of interest.

8. An acoustic microscope as in claim 3 in which both of said heating means are focused at the point of interest.

9. An acoustic microscope as in claim 3 in which said means for receiving said generated acoustic waves and providing an output signal is focused at the point of interest.

10. An acoustic microscope as in claim 3 in which one of said first and second heating means has a high intensity and the other a low intensity.

11. An acoustic microscope as in claim 10 in which the low intensity heating means it a current source.

12. An acoustic microscope as in claim 10 in which the low intensity heating means is a focused electron beam.

13. An acoustic microscope as in claim 1 in which said means for sensing the mixed expansion comprises means for directing acoustic waves at the region of interest and receiving acoustic waves reflected from said region.

14. An acoustic microscope as in claim 13 wherein said acoustic waves are modulated at a selected frequency.

15. An acoustic microscope as in claim 14 in which said sensing means includes means for providing an output signal representative of reflected acoustic waves at said selected frequency.

16. An acoustic microscope as in claim 15 in which said first means for heating heats the object at a fist frequency and said output signal is at the sum or difference frequency of said selected frequency and said first frequency.

17. An acoustic microscope as in claim 15 in which said second means for heating heats the object at a second frequency and said output signal is at the sum or difference frequency of said selected frequency and said second frequency.

18. An acoustic microscope as in claim 13 in which at least one of said heating means is found at the point of interest.

19. An acoustic microscope comprising
    first means for heating an object of interest at a first frequency so that the object thermally expands and generates acoustic waves at a first frequency,
    second means for heating the object of interest at a second frequency so that the object thermally expands and generates acoustic waves at a second frequency and
    means for receiving said generated acoustic waves and providing an output signal representative of the product of said acoustic waves.

20. An acoustic microscope as in claim 19 in which said means for receiving the generated acoustic waves provides an output representative of the sum or difference frequency of said acoustic waves.

21. An acoustic microscope as in claim 19 in which one of said acoustic wave frequencies is zero.

22. An acoustic microscope as in claim 19 when at least one of said heating means is focused on the point of interest.

23. An acoustic microscope as in claim 22 in which said means for receiving said generated acoustic waves and providing an output signal is focused at said point of interest.

24. An acoustic microscope as in claim 19 in which both of said heating means are focused at the point of interest.

25. An acoustic microscope as in claim 19 in which said means for receiving said generated acoustic waves and providing an output signal is focused at the point of interest.

26. An acoustic microscope as in claim 19 in which one of said heating means has a high intensity and the other a low intensity.

27. An acoustic microscope as in claim 26 in which the low intensity heating means is a current source.

28. An acoustic microscope as in claim 26 in which the low intensity heating means is a focused electron beam.

29. The method of acoustically inspecting an object of interest at a point of interest comprising heating the point of interest at two different frequencies to generate mixed acoustic waves and receiving said mixed acoustic waves and providing an output signal representative of their product.

30. The method of inspecting an object of interest at a point of interest comprising heating the point of interest with first background energy and heating the point of interest with inspection energy whereby the action of said combined energies generates a detectable acoustic wave, and sensing the acoustic wave radiated at said point of interest to form a representative signal.

31. The method as in claim 30 in which elastic movement at said point of interest is sensed.

* * * * *